United States Patent [19]

Hardtmann

[11] 4,117,137

[45] Sep. 26, 1978

[54] 2-AMINO-PYRIDYL NITROMETHYLKETONES AND 2-AMINO-PHENYL NITROMETHYLKETONES

[75] Inventor: Goetz E. Hardtmann, Morristown, N.J.

[73] Assignee: Sandoz, Inc., E. Hanover, N.J.

[21] Appl. No.: 813,266

[22] Filed: Jul. 6, 1977

Related U.S. Application Data

[63] Continuation-in-part of Ser. No. 724,990, Sep. 20, 1976, abandoned.

[51] Int. Cl.$^2$ ............................................. A61K 31/44
[52] U.S. Cl. ................................... 424/263; 424/330; 544/93; 544/94; 260/296 R; 260/577
[58] Field of Search .......................... 260/296 R, 577; 424/263, 330

[56] References Cited

PUBLICATIONS

Seter, abst. no. 28479z, vol. 66 of Chemical Abstracts (1967) (Abst. of Seter, Israel J. Chem., vol. 4, pp. 7–22 (1966–unavailable to Examiner in charge).
Beckwith et al., Chem. Abstracts, vol. 70, abst. no. 11669w (1969) (abst. of Beckwith et al., J. Chem. Soc., C 1968, pp. 2756–2759).
Beckwith, Chem. Abstracts, vol. 74, abst. no. 76430p (1971) (abst. of Beckwith, Ger. Offen. 1,926,475).
Sandison et al., Chem. Abstracts, vol. 82, abst. 72911p (1975).
Alessandrini et al., J. Chem. Soc. Dalton Trans. 1973, pp. 2409–2413.

*Primary Examiner*—John D. Randolph
*Attorney, Agent, or Firm*—Gerald D. Sharkin; Richard E. Vila; Frederick H. Weinfeldt

[57] ABSTRACT

2-Amino-3-pyridyl (or phenyl) nitromethylketones are prepared eg by reacting a 3,4-dihydro-1,3-dioxo-1H-pyrido [2,3-d][1,3]oxazine (a 3-azaisatoic anhydride) with the carbanion resulting from the reaction of nitromethane with a porton abstracting agent. The compounds are useful as anti-allergic agents.

45 Claims, No Drawings

2-AMINO-PYRIDYL NITROMETHYLKETONES AND 2-AMINO-PHENYL NITROMETHYLKETONES

This is a continuation in part of copending application Ser. No. 724,990 (filed Sept. 20, 1976), now abandoned.

The invention relates to chemical compounds which are 2-amino-3-pyridyl or phenyl nitromethylketones, to their preparation and to their use as pharmacological agents, particularly as anti-allergicc agents.

The compounds of the present invention are either a) free bases which may be represented by the following structural formula I:

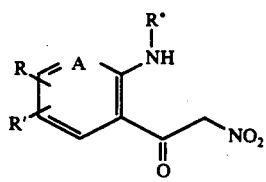

wherein A is either
a) N; or
b) CH and

R and R' are, when A is CH, independently hydrogen, halo of atomic weight of from 18 to 80, i.e., fluoro, chloro or bromo, alkyl of 1 to 4 carbon atoms, alkoxy of 1 to 4 carbon atoms, or trifluoromethyl, or R and R' together form 4,5-methylenedioxy and, when A is N, independently hydrogen or alkyl of 1 to 4 carbon atoms, R° is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

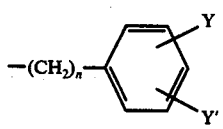

wherein
$n$ is 0 or 1, and
Y and Y' are indpendently hydrogen, halo of atomic weight of from 18 to 80, i.e., fluoro, chloro or bromo, alkyl of 1 to 3 carbon atoms, alkoxy of 1 to 3 carbon atoms or trifluoromethyl, and with the proviso that the unsaturation in any alkenyl or alkynyl is on other than the alpha carbon atom; or b) a salt form thereof, particularly a pharmaceutically acceptable salt thereof.

It will be appreciated that depending upon the type of A unit present, the compounds may be of either of two classes, ie Compounds Ia, when A is of type a) (pyridyl-type) and Compounds Ib when A is of type b) (phenyl type) the free bases of which may be represented by the formulae:

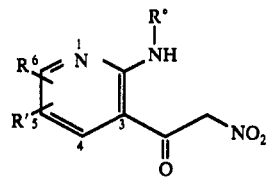

in which R, R' and R° are as defined above for type a); and

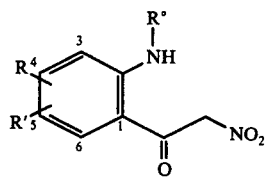

in which R, R' and R° are as defined above for type b).

The compounds of the formula I may be prepared by reacting a compound of the formula II:

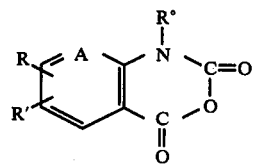

wherein R°, R, A and R' are as defined, with a compound of the formula III:

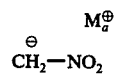

wherein $M_a^\oplus$ is a cation derived from a proton abstracting agent, in the presence of an inert organic solvent, the resulting reaction product being treated with a proton source when the compound in free base form is desired.

The preparation of Compounds I by reacting a Compound II with a Compound III may be carried out at temperatures generally in the range of from 0° C. to 150° C. in an inert organic solvent of conventional type, desirably an aprotic solvent, and under essentially anhydrous conditions. Examples of preferred solvents include dimethylacetamide, dimethylformamide, dimethylsulfoxide and tetrahydrofuran, more preferably dimethylsulfoxide. Preferred temperatures are generally in the range of from 10° C. to 100° C. The mol ratio of Compound III to Compound II is not critical and is suitably in the range of 0.8:1 to 3:1, preferably from about 1:1 to 2:1. Reaction times may vary fairly widely and can be typically of the order of 30 minutes to 30 hours, more usually 1 to 20 hours. The reaction product of the Compounds Ii and III is a salt form of the Compound I with the cation $M_a^\oplus$. Such reaction product is treated in a conventional manner with a proton source to readily obtain, if desired, the Compounds I in free base form. A wide variety of proton sources are known and may be employed, but it is generally preferred to employ aqueous mineral acid such as hydrochloric acid. The product of the formula I in free base or salt form may be isolated and recovered from the resulting reaction mixture by working up by conventional techniques including, without limitation, crystallization, distillation and gas and column chromatography.

The compound of the formula III is prepared in situ by reacting the compound (nitromethane) of the formula IIIA:

, $CH_3-NO_2$            IIIA with a proton abstracting agent in an organic solvent which is of the type suitable for the reaction of Compounds II and III. Reaction temperatures may be generally of the order of from minus 100° C. to plus 150° C., but are preferably in the range of from 10° C. to 50° C. The proton abstracting agents are those which will dislodge a hydrogen atom from the methyl group of Compounds IIIA to result in the ionic product III with which the Compound II reacts to yield the desired Compound I. Such agents are of well known types and are represented by a variety of chemical bases such as the alkali metal hydrides, the butyl lithiums and alkali metal carbonates, with the alkali metal carbonates being particularly preferred, e.g., potassium carbonate. In general, the salt forms of the compounds I are preferably alkali metal salt forms, particularly sodium or potassium, more preferably potassium. The phrase "derived from a proton abstracting agent" as used herein is meant to designate the cation present in the proton abstracting agent and freed as a result of the reaction with the Compound IIIA, e.g., potassium when potassium carbonate is used. The mol ratio of abstracting agent to the Compounds III may vary fairly widely but is most suitably at least about 0.8 to 1 and between 0.9:1 to 1.5:1 in the preferred modes of conducting the reaction.

As will be evident, the Compounds I may be prepared in accordance with the reactions above-described by combining Compounds II, IIIA and a proton abstracting agent in an organic solvent and either: (i) regulating the temperature to form the Compound III without substantial reaction with Compound II followed by increasing the temperature to form the Compound I; or (ii) establishing a temperature within the range of from 0° C. to 150° C., whereby the Compounds I are prepared simultaneously with and in the presence of the formation of Compounds III. It is generally convenient to prepare the compounds I simultaneously with the reaction by which the compounds III are prepared.

When preparing Compounds I in salt form by the method of this invention, it is, of course, convenient and preferred to employ a proton abstracting agent which will result directly in a pharmaceutically acceptable salt form, e.g., lithium, sodium or potassium. In cases in which it may be desired to employ a proton abstracting agent which will not provide or result in a pharmaceutically acceptable cation or in which it is desired to replace one pharmaceutically acceptable cation for another, such cation may be exchanged for the desired pharmaceutically acceptable cation by conventional and well known salt exchange procedures. Similarly, the free base forms may be converted to the salt forms by conventional treatment with a base, e.g. sodium hydroxide or potassium hydroxide. It will be recognized by those skilled in the art that the salts of the compounds of the formula I may be formed by virtue of the essentially acidic methylene bridging group between the nitro and ketone functions and may be represented in aqueous media by essentially tautomeric structures. The presence of the keto function in the free base forms may be confirmed by routine analysis in common organic solvents. In general, the free base forms are preferred.

The compounds of the formula II and IIIA are each either known per se or may be prepared from known materials by procedures established for the known compounds.

The preferred compounds of the formula I are generally those of type (a), i.e. A is N, and such compounds preferably have one or both of the features: (i) R° being alkyl, particularly methyl, or alkenyl, particularly allyl; and (ii) R being alkyl, particularly 6-alkyl, especially 6-methyl, and R' being hydrogen or alkyl, particularly methyl, but more preferably hydrogen.

The preferred compounds of the type (b), i.e. A is CH, are those having one or both of the features: (i) R° is alkyl, particularly methyl, or alkenyl, particularly allyl; and (ii) R and R' being from the group of hydrogen, halo, alkyl and alkoxy, more preferably alkyl and alkoxy, and most preferably both are alkoxy, particularly 4,5-dialkoxy, and especially 4,5-dimethoxy. A further subgrouping of the compounds Ib are those in which R and R' together form 4,5-methylenedioxy.

The compounds of formula I are useful because they possess disodium chromoglycate (DSCG)-like activity, in particular histamine release inhibiting activity, and are therefore useful in the treatment of allergic conditions, such as allergic asthma, as indicated in the passive cutaneous anaphylaxis test in the rat. Female rats (180–200 g) are sensitised by subcutaneous administration of 1 mg of egg albumin (Merck Nr. 967) and 200 mg. $Al(OH)_3$ in 1 ml. of physiological saline and 0.5 ml. of Haemophiluspertussis vaccine (Schweizerisches Serum and Impfinstitut, Bern; Nr. 115 325; $4 \times 10^{10}$ organism/ml) intraperitoneally. Fourteen days later, the animals are exsanguinated, the blood centrifuged, the serum collected and deep frozen. The serum thus obtained (anti-serum) is injected intradermally (0.1 ml of a 1:200 diluted serum per injection site) at four sites on the backs of untreated, female rats. Twenty-four hours later each rat is administered 0.1 to 5.6 mg/kg i.v. or 0.1 to 100 mg/kg p.o. of the test compound, and either immediately or 5 or 30 minute afterwards, in the case of intravenous administration, or 15 or 60 minutes afterwards, in the case of oral administration, afterwards egg albumin (5mg/ml i.v.) dissolved in physiological saline containing 0.25% Evans Blue dye (Merck Nr. 3169). The egg albumin elicits a cutaneous anaphylactic reaction, the intensity of which is proportional to the extent to which the Evans Blue dye diffuses into the tissue surrounding each of the four sensitisation sites. Thirty minutes after the administration of the egg albumin, the rats are killed with ether, the underside of the skin of the back of each animal is exposed and the diameter of the area of blue dye surrounding each of the four sensitisation sites are measured. Each dose of test compound is investigated in between four and six rats and the mean diameter compared with the mean value obtained in four solvent-treated control rats. The percentage inhibition is taken as the percentage of the mean diameter in the test animals relative to the mean diameter in the controls.

The DSCG-like activity, in particulr histamine release inhibiting activity, can be confirmed by inhibition of histamine release in the rate peritoneal mast cell test, basically as described by Kusner et al., J. Pharmacol. Exp. Therap. 184, 41–46 (1973), with the following modification: after sedimentation of the mast cells by centrifugation at $350 \times g$ and 4° C, the sediments are taken up in 1 ml of Hank's balanced salt solution (HBSS) (buffered to a pH of 6.9) and pooled. The resulting suspension is centrifuged, washed again with HBSS and sedimented. The thus purified mast cells are prepared as 2 ml suspensions in HBSS. To these are added either 2 ml of HBSS, to determine the spontaneous histamine release, or 2 ml of HBSS and 2.24 ug of compound 48/80 (N-methylhomoanisylamineformaldehyde condesate: a histamine liberator from Burroughs Wellcome and Co. Inc., Tuckahoe, N.Y. USA) to determine the 48.80 induced histamine release, or 2 ml of HBSS with 2.24 ug of 48/80 and from 18 to 180 ug/ml of the test compound, to determine the 48/80 induced histamine release in the presence of the test compound.

The 48/80 induced histamine release minus the spontaneous histamine release is taken as 100% histamine release. The 48/80 induced histamine release in the presence of the test compound minus the spontaneous histamine release is then compared with the 100% value to determine the percentage inhibition by the test compound. [The histamine determination is effected in conventional manner, for example as described in the above-mentioned Kusner et al. article, or in Kusner and Herzig, Advances in Automated Analysis, 429 (1971)].

For the above-mentioned use, the dosage administered will, of course, vary depending on the compound employed, mode of administration and treatment desired at a daily dosage of from about 0.3 to 100 mg/kg in animal body weight, conveniently given in divided doses two to four times daily, or in sustained release form. For the larger mammals, the total daily dosage is in the range of from about 20 to 400 mg of the compound admixed with a solid or liquid pharmaceutical carrier of conventional type, and divided dosage forms comprise 5 to 200 milligrams of the compound in admixture with a solid or liquid pharmaceutical carrier. As will be appreciated by those skilled in the art, the treatment of allergic conditions according to the invention is based on histamine release inhibition activity and is therefore essentially symptomatic. The ability to employ such compounds in the prophylactic treatment of such allergic conditions (as evident from the DSCG-like activity) is a desirable feature. However, the good oral activity relative to DSCG is a further feature.

Pharmaceutical compositions provided by the invention and useful for treating allergic conditions due to histamine release contain a compound of the formula I (in free acid or salt form) as active ingredient and one or more conventional pharmaceutically acceptable carriers, and such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compounds may also be administered by inhalation therapy techniques in compositions conventionally prepared and adapted for such procedures. In general, the compositions of the invention adapted for either oral, inhalation or parenteral administration may contain from 1% to 90% by total weight of active ingredient in combination with the carrier, more usually 3% to 70%. The preferred unit dosage forms are the essentially solid forms adapted for oral administration, e.g., tablets or capsules.

A representative formulation for administration 2 to 4 times a day for prophylatic treatment of allergic asthma is a capsule prepared by standard techniques to contain the following:

| Ingredients | Weight (mg) | |
|---|---|---|
| | A | B |
| 2-methylamino-6-methyl 3-pyridyl nitromethylketone | 30 | — |
| 2-methylamino- 3-pyridyl nitromethylketone | — | 30 |
| Kaolin | 210 | 210 |

In the following Examples all temperatures are in centigrade and room temperature is 20° to 30° C., unless indicated otherwise. The following examples are given for purposes of illustration only.

EXAMPLE 1

2-Methylamino-3-pyridyl nitromethylketone and potassium salt

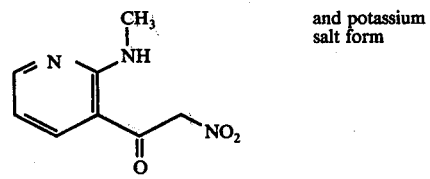

and potassium salt form

A mixture of 5.3 g of nitromethane, 10.6 g of potassium carbonate, 10.0 g of 4-methyl-3,4-dihydro-1,3-dioxo-1H-pyrido[2,3-d][1,3]oxazine and 150 ml. of dimethylsulfoxide is stirred at 20°–25° C. for 5 hours, diluted with cold water and washed three times with methylene chloride to obtain an aqueous solution of 2-methylamino-3-pyridyl nitromethylketone potassium salt.

The above-obtained potassium salt solution is neutralized with 2N hydrochloric acid to obtain a precipitate which is recovered by filtering, dried by suction, chromatographed using chloroform and the product crystallized from methylene chloride/ethanol to obtain 2-methylamino-3-pyridyl nitromethylketone, m.p. 156–159° C.

EXAMPLE 2

Following the procedure of Example 1, the following compounds of the invention are prepared.

A. 2-allylamino-3-pyridyl nitromethylketone;
B. 2-propargylamino-3-pyridyl nitromethylketone;
C. 2-cyclopropylmethylamino-3-pyridyl nitromethylketone;
D. 2-phenylamino-3-pyridyl nitromethylketone;
E. 2-benzylamino-3-pyridyl nitromethylketone;
F. 2-(p-fluorobenzylamino)-3-pyridyl nitromethylketone;
G. 2-methylamino-6-methyl-3-pyridyl nitromethylketone m.p. 209°–215° (decomposed);
H. 2-amino-6-methyl-3-pyridyl nitromethylketone;
I. 2-allylamino-6-methyl-3-pyridyl nitromethylketone; and
J. 2-methylamino-5,6-dimethyl-3-pyridyl nitromethylketone.

EXAMPLE 3

2-Allylamino-4,5-dimethoxyphenyl nitromethylketone* and potassium salt

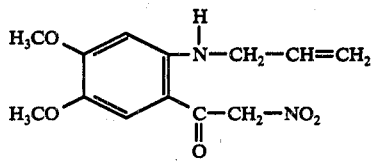

A mixture of 2.0 g of N-allyl-4,5-dimethoxyisatoic anhydride, 700 mg. of nitromethane, 1.1 g of potassium carbonate and 25 ml. of dimethylsulfoxide is stirred at room temperature for 18 hr; after which period some starting material may be found to remain unreacted. The mixture is then heated with stirring at 50° to 60° C. for 4 hr. The title product is then recovered from its potassium salt form by pouring the reaction mixture into cold water, then acidifying the diluted mixture by careful addition of 2N hydrochloric acid, and extracting with ethyl acetate. The combined ethyl acetate extracts are then washed twice with water, once with saturated sodium chloride solution, and then dried over anh. sodium sulfate, and solvent removed by evaporation to obtain an oily residue. The residue is then chromatographed on a column of silica gel using 1% methanol in chloroform, and the crude product crystallized from ethanol to obtain the refined title product m.p. 80°–82° C. (decomposed).

*May also be called 2'-allylamino-4',5' dimethoxy 2-nitroacetophenone.

Repeating the procedure of this example, using appropriate starting materials there is accordingly obtained:

A. 2-Allylaminophenyl nitromethylketone, m.p. 97°–100°;
B. 2-methylaminophenyl nitromethylketone, m.p. 115°–118°;
C. 2-cyclopropylmethylaminophenyl nitromethylketone;
D. 2-phenylaminophenyl nitromethylketone;
E. 2-benzylaminophenyl nitromethylketone;
F. 2-(p-fluorobenzylaminophenyl nitromethylketone, m.p. 102°–105°;
G. 2-aminophenyl nitromethylketone, m.p. 109°–111°;
H. 2-propargylaminophenyl nitromethylketone; m.p. 136°–139°;
I. 2-methylamino-4,5-methylenedioxyphenyl nitromethylketone, m.p. 180°–182°.
J. 2-methylamino-4,5-dimethoxyphenyl nitromethylketone.

What is claimed is:

1. A compound selected from the group consisting of:
a) a nitromethylketone in free base form of the formula:

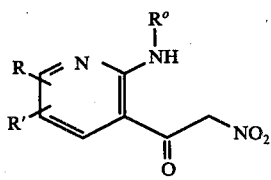

wherein

R° is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms or

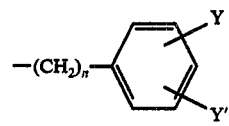

n is 0 or 1,
Y and Y' are independently hydrogen, fluoro, chloro, bromo, alkyl of 1 to 3 carbon atoms, alkoxy of 1 to 3 carbon atoms or trifluoromethyl, and
R and R' are independently hydrogen or alkyl of 1 to 4 carbon atoms, with the proviso that the unsaturation in any alkenyl or alkynyl is other than on the alpha carbon atom; and b) a salt form thereof.

2. A compound of claim 1 in which the salt form is formed by a pharmaceutically acceptable cation.
3. A compound of claim 2 in which R° is alkyl.
4. A compound of claim 2 in which R° is alkenyl.
5. A compound of claim 2 in which R° is alkynyl.
6. A compound of claim 2 in which R° is cycloalkyl.
7. A compound of claim 2 in which R° is cycloalkylalkyl.
8. A compound of claim 2 in which R° is

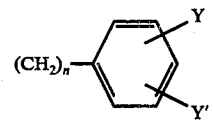

9. A compound of claim 8 in which n is 0.
10. A compound of claim 8 in which n is 1.
11. A compound of claim 1 in free base form.
12. A compound of claim 2 in which R° is allyl and R and R' are hydrogen.
13. A compound of claim 2 in which R° is methyl and R and R' are each hydrogen.
14. A compound of claim 2 in which R° is methyl, R is 6-methyl and R' is hydrogen.
15. A compound of claim 2 in which R° is allyl, R is 6-methyl and R' is hydrogen.
16. A compound of claim 2 in which R° is alkyl or allyl.
17. A compound of claim 16 in which R° is methyl or allyl.
18. The compound of claim 12 in free base form.
19. The compound of claim 13 in free base form.
20. The compound of claim 14 in free base form.
21. The compound of claim 15 in free base form.
22. The method of treating allergic conditions due to histamine release comprising administering to a mammal in need of such treatment an allergy treating effective amount of a compound of claim 2.
23. A pharmaceutical composition comprising an inert pharmaceutically acceptable carrier and an allergy treating effective amount of a compound of claim 2.
24. The method of claim 22 in which the compound is a compound in which R° is alkyl or allyl.
25. The method of claim 24 in which R° is methyl or allyl.
26. The method of claim 24 in which R° is methyl and R and R' are hydrogen.

27. The method of claim 24 in which R° is methyl, R is 6-methyl and R' is hydrogen.

28. The method of claim 24 in which R° is allyl and R and R' are hydrogen.

29. The method of claim 24 in which R° is allyl, R is 6-methyl and R' is hydrogen.

30. The method of claim 22 in which the compound is in free base form.

31. The process for preparing a compound of claim 1 comprising reacting a compound of the formula:

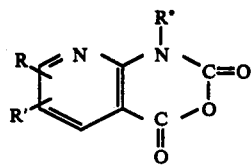

wherein R°, R and R' are as defined in claim 1, with a compound of the formula:

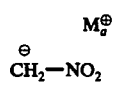

wherein $M_a$ is a cation derived from a proton abstracting agent, in the presence of an inert organic solvent at a temperature in the range of from 0° C. to 150° C. and; (a) when the free base form is desired, treating the resulting product with a proton source; and (b) exchanging $M_a$ for a pharmaceutically acceptable cation when the latter is desired and not represented by $M_a$.

32. A compound which is either (a) a free base of the formula:

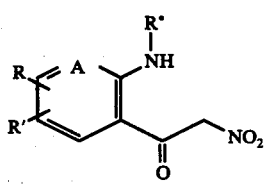

wherein A is either
a. N; or
b. CH; and

R and R' are, when A is CH, independently hydrogen, fluoro, chloro or bromo, alkyl of 1 to 4 carbon atoms, alkoxy of 1 to 4 carbon atoms, or trifluoromethyl, or R and R' together form, 4,5-methylenedioxy and, when A is N, independently hydrogen or alkyl of 1 to 4 carbon atoms, R° is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

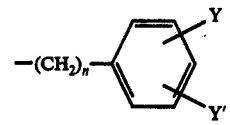

wherein n is 0 or 1, and

Y and Y' are independently hydrogen, fluoro, chloro or bromo, alkyl of 1 to 3 carbon atoms, alkoxy of 1 to 3 carbon atoms or trifluoromethyl, and with the proviso that the unsaturation in any alkenyl or alkynyl is on other than the alpha carbon atom; or (b) a salt form thereof.

33. A compound of claim 32 in which the salt form is formed by a pharmaceutically acceptable cation.

34. A compound of claim 32 in which A is CH.

35. The method of treating allergic conditions due to histamine release comprising administering to a mammal in need of such treatment an allergy treating effective amount of a compound of claim 33.

36. A pharmaceutical composition comprising an inert pharmaceutically acceptable carrier and an allergy treating effective amount of a compound of claim 33.

37. The process for preparing a compound of claim 32 comprising reacting a compound of the formula:

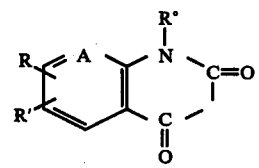

wherein A, R°, R and R' are as defined in claim 32, with a compound of the formula:

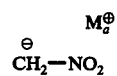

wherein $M_a$ is a cation derived from a proton abstracting agent, in the presence of an inert organic solvent at a temperature in the range of from 0° C. to 150° C. and; (a) when the free base form is desired, treating the resulting product with a proton source; and (b) exchanging $M_a$ for a pharmaceutically acceptable cation when the latter is desired and not represented by $M_a$.

38. A compound of claim 34 which is in free base form.

39. A compound of claim 34 in which R° is allyl, R is 4-methoxy and R' is 5-methoxy.

40. A compound of claim 34 in which R° is allyl, and each of R and R' is a hydrogen atom.

41. A compound of claim 34 in which R° is methyl and each of R and R' is a hydrogen atom.

42. A compound of claim 34 in which R is methyl and R and R' represent a 4,5-methylenedioxy radical.

43. A compound of claim 34 in which R° is p-fluorophenyl and each of R and R' is a hydrogen atom.

44. A compound of claim 34 in which each of R°, R and R' is a hydrogen atom.

45. A compound of claim 34 in which R° is propargyl and each of R and R' is a hydrogen atom.

* * * * *